United States Patent
Hayashi et al.

(10) Patent No.: US 12,285,514 B2
(45) Date of Patent: *Apr. 29, 2025

(54) COSMETIC COMPOSITION

(71) Applicant: KAO CORPORATION, Tokyo (JP)

(72) Inventors: Kaori Hayashi, Shiroi (JP); Masayuki Narita, Ichikawa (JP); Naoya Kawakami, Chiba (JP); Tomokazu Iseki, Izumiotsu (JP)

(73) Assignee: KAO CORPORATION, Tokyo (JP)

( * ) Notice: Subject to any disclaimer, the term of this patent is extended or adjusted under 35 U.S.C. 154(b) by 785 days.

This patent is subject to a terminal disclaimer.

(21) Appl. No.: 17/598,378

(22) PCT Filed: Mar. 26, 2020

(86) PCT No.: PCT/JP2020/013861
§ 371 (c)(1),
(2) Date: Sep. 27, 2021

(87) PCT Pub. No.: WO2020/203704
PCT Pub. Date: Oct. 8, 2020

(65) Prior Publication Data
US 2022/0151909 A1    May 19, 2022

(30) Foreign Application Priority Data
Apr. 2, 2019 (JP) .................. 2019-070891

(51) Int. Cl.
*A61K 8/81* (2006.01)
*A61K 8/34* (2006.01)
*A61Q 5/06* (2006.01)

(52) U.S. Cl.
CPC .......... *A61K 8/8158* (2013.01); *A61K 8/8147* (2013.01); *A61K 8/8152* (2013.01);
(Continued)

(58) Field of Classification Search
CPC .. A61K 8/8158; A61K 8/8147; A61K 8/8152; A61K 2800/5422; A61Q 5/06
See application file for complete search history.

(56) References Cited

U.S. PATENT DOCUMENTS

| | | |
|---|---|---|
| 2002/0115780 A1 | 8/2002 | Mougin |
| 2002/0159965 A1 | 10/2002 | Frechet et al. |

(Continued)

FOREIGN PATENT DOCUMENTS

| | | |
|---|---|---|
| JP | 2003286142 A | 10/2003 |
| JP | 2003335637 A | 11/2003 |

(Continued)

OTHER PUBLICATIONS

Jachowicz, "Anaylsis of Polymers for Cosmetics," International Federation Societies of Cosmetic Chemists (IMFCC), 2004, pp. 1-295. (Year: 2004).*

(Continued)

*Primary Examiner* — Kyung S Chang
(74) *Attorney, Agent, or Firm* — Element IP, PLC (57) ABSTRACT

The present invention relates to a cosmetic composition containing the following Components (A) and (B): Component (A): a hydrophobic polymer which has a glass transition temperature Tg of 30° C. or higher, the polymer having a different kind of an electric charge to the following Component (B), or not having an electric charge; and Component (B): a hydrophilic ionic polymer. The cosmetic composition of the present invention can be suitably used in cosmetics for hair.

9 Claims, 2 Drawing Sheets

(52) U.S. Cl.
CPC ........ *A61Q 5/06* (2013.01); *A61K 2800/5422* (2013.01); *A61K 2800/5424* (2013.01); *A61K 2800/5426* (2013.01)

(56) References Cited

U.S. PATENT DOCUMENTS

| | | |
|---|---|---|
| 2004/0009136 A1 | 1/2004 | Dubief et al. |
| 2004/0096474 A1 | 5/2004 | Merlau et al. |
| 2007/0166250 A1 | 7/2007 | Hiwatashi et al. |
| 2011/0067721 A1 | 3/2011 | Tate et al. |

FOREIGN PATENT DOCUMENTS

| | | |
|---|---|---|
| JP | 2003534264 A | 11/2003 |
| JP | 2004002432 A | 1/2004 |
| JP | 2004510719 A | 4/2004 |
| JP | 2004168776 A | 6/2004 |
| JP | 2020169164 A | 10/2020 |
| JP | 2020189807 A | 11/2020 |
| JP | 2020200244 A | 12/2020 |

OTHER PUBLICATIONS

CAS 9011-16-9 Poly(methyl vinyl ether-alt-maleic anhydride)—Alfa Chemistry (last access date: Jan. 17, 2025) (Year: 2025).*
International Search Report issued Jun. 9, 2020 in PCT/JP2020/013861, 3 pages.
Extended European Search Report issued Aug. 9, 2023 in Patent Application No. 20781977.2, 15 pages.

* cited by examiner

COSMETIC COMPOSITION

FIELD OF THE INVENTION

The present invention relates to a cosmetic composition, cosmetics, and a method of hair styling.

BACKGROUND OF THE INVENTION

In conventional hair styling, a method of maintaining styling including forming a coating film on hair surfaces, to provide strength of the coating film has been adopted. However, when a coating film is made firm in order to increase the styling property, there are some disadvantages that the coating films are more likely to come off by impacts of contacting or the like of hairs per se in daily lives. In order to improve the disadvantages, Patent Publication 1 shows an example of a styling composition which is formed into a thick film or gel with an amphophilic linear block copolymer containing a hydrophilic block and a hydrophobic block, and Patent Publication 2 shows an example of improving styling property and flexibility of a coating film using a block polymer having a rigid constituting unit and a soft constituting unit, each unit having a different Tg, when formed as a polymer.

However, in these methods, there are some disadvantages that the setting properties of the hair are lowered under the high humidity conditions. In view of the above, Patent Publication 3 provides a block polymer having a relatively high binding strength under relatively high humidity conditions due to the functions of blocks having different Tg's as a cosmetic or personal care-composition, each containing a thermoplastic elastomer used as a film-forming polymer, and a diluent or a carrier which is acceptable in cosmetics.

Patent Publication 1: Japanese Patent Laid-Open No. 2004-2432
Patent Publication 2: Japanese Unexamined Patent Publication No. 2003-534264
Patent Publication 3: Japanese Unexamined Patent Publication No. 2004-510719

SUMMARY OF THE INVENTION

However, in conventional polymers, when impacts are applied due to contacting or the like of hairs themselves after hair styling under the high-humidity conditions, the holding of the hair setting cannot be sufficiently guaranteed.

The present invention relates to the provisions of a cosmetic composition having excellent retentiveness and impact resistance of the hair setting under the high-humidity conditions, and cosmetics, and a method of hair styling including applying the cosmetic composition to hair.

The present invention relates to the following [1] and [2]:

[1] A cosmetic composition containing the following Components (A) and (B):

Component (A): a hydrophobic polymer which dissolves in ethanol at 25° C. in an amount of 1% by mass or more, and has a glass transition temperature Tg of 30° C. or higher, the polymer having a different kind of an electric charge to the following Component (B), or not having an electric charge; and Component (B): a hydrophilic ionic polymer which dissolves in ethanol at 25° C. in an amount of 1% by mass or more.

[2] A method of hair styling, including applying a cosmetic composition as defined in [1] to hairs.

DETAILED DESCRIPTION OF THE INVENTION

According to the present invention, a cosmetic composition and cosmetics having excellent retentiveness and impact resistance of the hair setting under high-humidity conditions, and a method of hair styling including applying the cosmetic composition to hairs can be provided.

[Cosmetic Composition]

The cosmetic composition of the present invention contains the following Components (A) and (B):

Component (A): a hydrophobic polymer which dissolves in ethanol at 25° C. in an amount of 1% by mass or more, and has a glass transition temperature Tg of 30° C. or higher, the polymer having a different kind of an electric charge to the following Component (B), or not having an electric charge; and Component (B): a hydrophilic ionic polymer which dissolves in ethanol at 25° C. in an amount of 1% by mass or more.

Components (A) and (B) are each a polymer which dissolves in ethanol at 25° C. in an amount of 1% by mass or more.

The hydrophilic polymer as used herein refers to a polymer having transmittance in accordance with the following measurement method of 80% or more, and the hydrophobic polymer as used herein refers to a polymer having transmittance in accordance with the following measurement method of less than 80%. Here, in a case where the polymer is a cationic polymer containing 30% by mass or more of the constituting units derived from methyl methacrylate in the polymer, the polymer is a hydrophobic polymer regardless of the transmittance.

(Preparation of Samples)

Water is added in an amount of 67 parts by mass, based on 100 parts by mass of an ethanol solution containing 10% by mass of the polymer (unneutralized), to provide a sample.

(Measurement Method)

The absorbance of the sample at 25° C. is measured with a spectrophotometer at 450 to 700 nm.

Here, when a sample is a neutralized product, the transmittance is measured after recovering a non-neutralized state according to the following procedures.

Instrument: A chromatograph tube having an inner diameter of 30 mm and a height of 300 mm (glass filter, with a stopper)

Resin: Dowex™ 50 W×8, 1.00 to 200 mesh strongly acidic cationic exchanging resin (H type), manufactured by FUJIFILM Wako Pure Chemical Corporation Amount of resin filled to the instrument: 60 g Procedures:

1. The resin was washed with ion-exchanged water, and then substituted with ethanol, and filled in the chromatograph tube.

2. Plascize L-9909B, manufactured by GOO CHEMICAL CO., LTD., was diluted with ethanol to a concentration of 20% by mass, and 20 g of the above sample was introduced in the resin-filled chromatograph tube. A resin layer was allowed to flow through the tube by deadweight, and an intended product (non-neutralized product) was collected from the bottom.

Although the mechanisms that the cosmetic composition of the present invention has excellent retentiveness and impact resistance of the hair setting (hereinafter both are also together referred to "hygroscopic resistance") under the high-humidity conditions are not elucidated, the mechanisms are assumed to be as follows. In the cosmetic composition of the present invention, Component (A) and Component (B) are incompatible due to the differences in polarities, so that, for example, the evaporation of the solvent is induced, thereby forming a layer-separation structure. Since a phase formed by Component (A) (a hydrophobic phase) would hardly absorb water in the air, the polymer is still rigid without undergoing plasticization. A phase formed by Component (B) (a hydrophilic phase) absorbs water in the air and undergoes plasticization, but exhibits both flexibility and toughness. By maintaining the styling by the coarseness of Component (A), and preventing a coating film from breaking by moderating the impacts by the flexibility and the toughness of Component (B), it is assumed that the hygroscopic resistance that is more excellent than those of the prior arts is exhibited.

[Component (A)]

Component (A) is a hydrophobic polymer which dissolves in ethanol at 25° C. in an amount of 1% by mass or more, and has a glass transition temperature Tg of 30° C. or higher. Component (A) may be any one of anionic polymers, cationic polymers, and nonionic polymers, and it is preferable that the polymer is an ionic polymer having a different kind of an electric charge to the following Component (B), from the viewpoint of enhancing the retentiveness of the hair setting under high-humidity conditions. Component (A) has the same electric charge as Component (B) indicating that Component (A) is a cationic polymer, if Component (B) is a cationic polymer, and Component (A) is an anionic polymer, if Component (B) is a anionic polymer. Specific examples include cationic polymers, anionic polymers, nonionic polymers, and the like described later, and more specific examples include a copolymer containing a polyacrylic acid-based polymer having an acrylic acid backbone, the copolymer containing a constituting unit derived from a monomer polymerizable with acrylic acid, the copolymer containing a constituting unit containing an acrylamide having a linear alkyl group having 1 or more carbon atoms and 12 or less carbon atoms or a branched alkyl group having 3 or more carbon atoms and 6 or less carbon atoms, or styrene, and even more specific examples include hydrophobic polymers or the like having constituting units mentioned later, from the viewpoint of maintaining styling. It is considered that Component (A) and Component (B) have different kinds of electric charge, so that Component (A) and Component (B) interact at the interface to form a crosslinked structure, thereby making them more excellent in hygroscopic resistance.

The glass transition point Tg of Component (A) is 30° C. or higher, preferably 40° C. or higher, more preferably 50° C. or higher, even more preferably 60° C. or higher, and still even more preferably 70° C. or higher, from the viewpoint of enhancing hygroscopic resistance, and the glass transition point is preferably 180° C. or lower, more preferably 150° C. or lower, and even more preferably 130° C. or lower, from the same viewpoint.

The weight-average molecular weight of Component (A) is preferably 5000 or more, more preferably 20000 or more, and even more preferably 100000 or more, from the viewpoint of enhancing hygroscopic resistance, and the weight-average molecular weight is preferably 500000 or less, more preferably 450000 or less, and even more preferably 350000 or less, from the viewpoint of enhancing hairwash removability. The method for measuring a weight-average molecular weight is as described in Examples set forth below.

The amount of the amine when Component (A) is a cationic polymer is preferably 1% by mass or more, more preferably 3% by mass or more, and even more preferably 5% by mass or more, from the viewpoint of enhancing hygroscopic resistance, and the amount of the amine is preferably 60% by mass or less, more preferably 45% by mass or less, and even more preferably 35% by mass or less, from the same viewpoint. The amount of the amine in Component (A) as used herein means an amount occupied by the constituting units having an amino group in the molecule, in the entire constituting units constituting Component (A).

The amount of the carboxylic acid when Component (A) is an anionic polymer is preferably 1% by mass or more, more preferably 3% by mass or more, and even more preferably 5% by mass or more, from the viewpoint of enhancing hygroscopic resistance, and the amount of the carboxylic acid is preferably 50% by mass or less, more preferably 35% by mass or less, even more preferably 30% by mass or less, and still even more preferably 20% by mass or less, from the same viewpoint. The amount of the carboxylic acid in Component (A) as used herein means an amount occupied by the constituting units having an carboxy group in the molecule, in the entire constituting units constituting Component (A).

The content of Component (A) in the cosmetic composition of the present invention is preferably 9% by mass or more, more preferably 33% by mass or more, and even more preferably 44% by mass or more, from the viewpoint of enhancing hygroscopic resistance, and the content is preferably 83% by mass or less, more preferably 75% by mass or less, and even more preferably 60% by mass or less, from the viewpoint of enhancing hygroscopic resistance and hairwash removability.

[Component (B)]

Component (B) is a hydrophilic ionic polymer which dissolves in ethanol at 25° C. in an amount of 1% by mass or more. Specific examples include hydrophilic cationic polymers, hydrophilic anionic polymers, and the like, which are mentioned later. From the viewpoint of enhancing hygroscopic resistance, more specific examples include a copolymer containing a polyacrylic acid-based polymer having an acrylic acid backbone, which is a copolymer containing a constituting unit derived from a monomer copolymerizable with acrylic acid and containing a constituting unit derived from a monomer having an amino group, and even more specific examples include hydrophilic polymers having constituting units mentioned later, and the like.

The glass transition point Tg of Component (B) is preferably 0° C. or higher, more preferably 10° C. or higher, even more preferably 25° C. or higher, and still even more preferably 40° C. or higher, from the viewpoint of enhancing hygroscopic resistance, and the glass transition point is preferably 130° C. or lower, more preferably 120° C. or lower, and even more preferably 100° C. or lower, from the same viewpoint.

The weight-average molecular weight of Component (B) is preferably 5000 or more, more preferably 20000 or more, and even more preferably 100000 or more, from the viewpoint of enhancing hygroscopic resistance, and the weight-average molecular weight is preferably 500000 or less, more preferably 450000 or less, and even more preferably 350000 or less, from the viewpoint of enhancing hairwash removability. The method for measuring a weight-average molecular weight is as described in Examples set forth below.

The amount of the amine when Component (B) is a cationic polymer is preferably 1% by mass or more, more preferably 3% by mass or more, and even more preferably 5% by mass or more, from the viewpoint of enhancing hygroscopic resistance, and the amount of the amine is preferably 60% by mass or less, more preferably 45% by mass or less, and even more preferably 35% by mass or less, from the same viewpoint. The amount of the amine in Component (B) as used herein means an amount occupied by the constituting units having an amino group in the molecule, in the entire constituting units constituting Component (B).

The amount of the carboxylic acid when Component (B) is an anionic polymer is preferably 1% by mass or more, more preferably 3% by mass or more, and even more preferably 5% by mass or more, from the viewpoint of enhancing hygroscopic resistance, and the amount of the carboxylic acid is preferably 50% by mass or less, more preferably 35% by mass or less, even more preferably 30% by mass or less, and still even more preferably 20% by mass or less, from the same viewpoint. The amount of the carboxylic acid in Component (B) as used herein means an amount occupied by the constituting units having an carboxy group in the molecule, in the entire constituting units constituting Component (B).

The content of Component (B) in the cosmetic composition of the present invention is preferably 17% by mass or more, more preferably 25% by mass or more, and even more preferably 40% by mass or more, from the viewpoint of enhancing hygroscopic resistance and hairwash removability, and the content is preferably 91% by mass or less, more preferably 67% by mass or less, and even more preferably 56% by mass or less, from the viewpoint of enhancing hygroscopic resistance.

In the cosmetic composition of the present invention, the mass ratio of Component (A) to Component (B) [Component (A)/Component (B)] is preferably 0.1 or more, more preferably 0.5 or more, and even more preferably 0.8 or more, from the viewpoint of enhancing hygroscopic resistance, and the mass ratio is preferably 5.0 or less, more preferably 3.0 or less, and even more preferably 1.5 or less, from the viewpoint of enhancing hygroscopic resistance and hairwash removability.

[Constituting Units that Constitute Components (A) and (B)]

In the present invention, Components (A) and (B) mentioned above are polymers of various monomers, and the constituting units may be any one of constituting units derived from hydrophobic unsaturated monomers or hydrophilic unsaturated monomers.

Specifically, the hydrophobic unsaturated monomer includes (meth)acrylates having a hydrocarbon group having 1 or more carbon atoms and 22 or less carbon atoms; acrylamides having a hydrocarbon group having 1 or more carbon atoms and 22 or less carbon atoms; halogenated olefins such as vinyl chloride, vinyl fluoride, vinylidene chloride, and vinylidene fluoride; olefins such as ethylene, propylene, and isobutylene; vinyl esters such as vinyl formate, vinyl acetate, vinyl propionate, and vinyl versatate; styrene; and the like.

The hydrophilic unsaturated monomers include nonionic unsaturated monomers, anionic unsaturated monomers, cationic unsaturated monomers, amphoteric unsaturated monomers, and the like.

The nonionic unsaturated monomers include (meth)acrylamides; hydroxy group-containing or ether group-containing (meth)acrylates such as hydroxyethyl (meth)acrylate, polyethylene glycol mono(meth)acrylate, and methoxypolyethylene glycol mono(meth)acrylate; and the like.

The anionic unsaturated monomers include carboxy group-containing unsaturated monomers such as (meth)acrylic acid, maleic acid, maleic anhydride, itaconic acid, crotonic acid, and 6-acrylamidehexanoate; sulfonate group-containing unsaturated monomers such as styrenesulfonic acid, 3-(methacryloyloxy)propanesulfonic acid, acrylamide propanesulfonic acid, and 2-acrylamide-2-methylpropanesulfonic acid: and the like.

These anionic unsaturated monomers can be used directly in the form of acids, or can be partially neutralized or completely neutralized and used. Alternatively, these monomers can be used directly in the form of acid when used in a copolymer, and the copolymer can then be partially neutralized or completely neutralized. The base used in the neutralization is, for example, an alkali metal hydroxide such as potassium hydroxide or sodium hydroxide; ammonia; an amine compound such as monoethanolamine, diethanolamine, triethanolamine, or trimethylamine.

The cationic unsaturated monomers include one or more members selected from unsaturated monomers having an amino group and unsaturated monomers having a quaternary ammonium base.

The unsaturated monomers having an amino group include N,N-dimethylaminoethyl (meth)acrylate, N,N-diethylaminoethyl (meth)acrylate, N,N-dimethylaminopropyl (meth)acrylate, N,N-diethylaminopropyl (meth)acrylate, N,N-dimethylaminoethyl (meth)acrylamide, N,N-diethylaminoethyl (meth)acrylamide, N,N-dimethylaminopropyl (meth)acrylamide, N,N-diethylaminopropyl (meth)acrylamide, 2-vinylpyridine, 4-vinylpyridine, and structures in which these monomers are neutralized with an acid represented by $H^+X^-$.

Here, $X^-$ is an anion including a halide ion such as a chloride ion or a bromide ion; an organic acid ion such as an alkyl sulfate ion of which alkyl moiety has 1 or more carbon atoms and 3 or less carbon atoms, an acetate ion, a lactate ion, a benzoate ion, an adipate ion, a formate ion, a malate ion, or a glycolate ion; or the like. The alkyl sulfate ion, the lactate ion, the formate ion, the malate ion, or the glycolate ion is preferred, and the lactate ion is more preferred, from the viewpoint of the feel of hair after setting when the hair is set with the hair cosmetics of the present invention, and the setting retentiveness under the high-humidity conditions.

In addition, the unsaturated monomers having a quaternary ammonium base include (meth)acryloyloxyethyl trimethylammonium, (meth)acryloyloxypropyl trimethylammonium, (meth)acryloylaminoethyl trimethylammonium, (meth)acryloylaminopropyl trimethylammonium, diallyl dimethylammonium, 1-ethyl-4-vinylpyridinium, 1,2-dimethyl-5-vinylpyridinium, and the like, each having $X^-$ as a counterion.

The amphoteric unsaturated monomers include compounds obtained by treating a cationic unsaturated monomer mentioned above with a denaturation agent such as a sodium or potassium haloacetate, and the like. Specific examples are N-(meth)acryloyloxyethyl-N,N-dimethylammonium-N-methylcarboxybetaine, N-(meth)acryloyloxyethyl-N,N-diethylammonium-N-methylcarboxybetaine, N-(meth)acryloyloxypropyl-N,N-dimethylammonium-N-methylcarboxybetaine, N-(meth)acryloyloxypropyl-N,N-diethylammonium-N-methylcarboxybetaine, methyl-2-vinylpyridinium carbonate, and methyl-4-vinylpyridinium carbonate.

In the present invention, it is preferable that Components (A) and (B) mentioned above have one or more groups selected from alkylamide groups and aminoalkylamide groups, from the viewpoint of enhancing hygroscopic resistance. In addition, it is preferable that the components have one or more constituting units selected from formulas 1, 2, and 3 given below are preferred, from the same viewpoint.

<Constituting Unit Represented by Formula 1>

The constituting unit represented by formula 1 as used herein has the following structure:

(formula 1)

wherein $R^1$ is a hydrogen atom or a methyl group; and each of $R^2$ and $R^3$ is independently a hydrogen atom or a hydrocarbon group having 1 or more carbon atoms and 12 or less carbon atoms which may have a substituent, with proviso that when either one of $R^2$ or $R^3$ is a hydrogen atom, the other is a hydrocarbon group having 1 or more carbon atoms and 12 or less carbon atoms, and when both $R^2$ and $R^3$ are not a hydrogen atom, they are hydrocarbon groups having a total number of carbon atoms of $R^2$ and $R^3$ of 2 or more and 24 or less;

alternatively, $R^2$ and $R^3$ may be bound to each other to form a ring structure, wherein a total number of carbon atoms of $R^2$ and $R^3$ in that case is 3 or more and 24 or less.

The constituting unit represented by formula 1 is a constituting unit which is derived by polymerizing an unsaturated monomer represented by formula 1' given below:

(formula 1')

wherein each of $R^1$, $R^2$ and $R^3$ in formula 1' are the same as those defined in formula 1.

The preferred substituents in formula 1 and formula 1' are as follows.

$R^1$ is a hydrogen atom or a methyl group. A hydrogen atom is more preferred, from the viewpoint of availability of the unsaturated monomers, and from the viewpoint of polymerizability of the monomers.

Each of $R^2$ and $R^3$ is independently a hydrogen atom or a hydrocarbon group having 1 or more carbon atoms and 12 or less carbon atoms which may have a substituent. The substituent in $R^2$ and $R^3$ includes a phenyl group, and the like, and it is preferable that each of $R^2$ and $R^3$ is a hydrogen atom or a hydrocarbon group having 1 or more carbon atoms and 12 or less carbon atoms.

When either one of $R^2$ or $R^3$ is a hydrogen atom, the other is a hydrocarbon group having 1 or more carbon atoms and 12 or less carbon atoms or an isobornyl group. A hydrocarbon group having 8 or less carbon atoms is preferred, and a hydrocarbon group having 6 or less carbon atoms is more preferred, from the viewpoint of improving dissolubility in a solvent contained in the cosmetics and hairwash removability.

When both of $R^2$ and $R^3$ are not a hydrogen atom, a total number of carbon atoms of $R^2$ and $R^3$ is 2 or more and 24 or less. A total number of carbon atoms is preferably 8 or less, and a total number of carbon atoms is more preferably 6 or less, from the viewpoint of improving dissolubility in a solvent contained in the cosmetics and hairwash removability.

In addition, each of $R^2$ and $R^3$ is preferably a linear or branched alkyl group, or a hydrocarbon group having a ring structure, and each is more preferably a linear or branched alkyl group, from the viewpoint of enhancing impact resistance under the high-humidity conditions.

When $R^2$ and $R^3$ are bound to each other to form a ring structure, a total number of carbon atoms of $R^2$ and $R^3$ is 3 or more and 24 or less. A total number of carbon atoms is preferably 8 or less, and a total number of carbon atoms is more preferably 6 or less, from the viewpoint of improving dissolubility in a solvent contained in the cosmetics and hairwash removability.

It is preferable that either one of $R^2$ or $R^3$ is a hydrogen atom, and the other is a hydrocarbon group having 4 or more carbon atoms and 24 or less carbon atoms, from the viewpoint of improving dissolubility in a solvent contained in the cosmetics and hairwash removability. Each of $R^2$ and $R^3$ is more preferably an alkyl group having 4 or more carbon atoms and 24 or less carbon atoms, even more preferably an alkyl group having 4 or more carbon atoms and 8 or less carbon atoms, still even more preferably an alkyl group having 4 carbon atoms, still even more preferably a branched alkyl group having 4 carbon atoms, and still even more preferably a tert-butyl group, from the viewpoint of enhancing impact resistance under the high-humidity conditions.

Specific examples of the unsaturated monomers represented by formula 1' include (meth)acrylamides such as dimethyl (meth)acrylamide, N-butyl (meth)acrylamide, N-isobutyl (meth)acrylamide, N-tert-butyl (meth)acrylamide, N-pentyl (meth)acrylamide, N-(2,2-dimethylpropyl) (meth)acrylamide, N-methyl-N-butyl (meth)acrylamide, N-ethyl-N-propyl (meth)acrylamide, N,N-dipropyl (meth)acrylamide, N-tert-octyl acrylamide, and isobornyl (meth)acrylamide.

The unsaturated monomers represented by formula 1' are preferably one or more members selected from N-butyl (meth)acrylamide, N-isobutyl (meth)acrylamide, and N-tert-butyl (meth)acrylamide, and more preferably N-tert-butyl (meth)acrylamide, from the viewpoint of enhancing impact resistance under the high-humidity conditions. Here, the term "(meth)acryl" as used herein means acryl, methacryl, or both.

<Constituting Unit Represented by Formula 2>

The constituting unit represented by formula 2 as used herein has the following structure:

(formula 2)

wherein R is a hydrogen atom or a methyl group;

if $X^1$ is an oxygen atom,

—$Y^1$—$X^2$ is a group selected from an alkyl group having 1 or more carbon atoms and 18 or less carbon atoms, an isobornyl group, —$(CH_2)_p$—$N(R^5)_2$, —$(CH_2)_p$—$OR^5$, —$C(CH_3)_2$—$N(R^5)_2$, and —$C(CH_3)_2$—$OR^5$, where p is 1 or more and 3 or less, and $R^5$ is a hydrogen atom or an alkyl group having 1 or more carbon atoms and 4 or less carbon atoms; or alternatively, $Y^1$ is a group containing 1 to 15 polyoxyalkylene groups having 2 or 3 carbon atoms, $X^2$ is a hydrogen atom, —$CH_3$, or —$C_2H_5$, or if $X^1$ is NH, $Y^1$ is an alkylene group having 1 or more carbon atoms and 3 or less carbon atoms, $X^2$ is —$N(R^5)_2$, wherein $R^5$ is a hydrogen atom or an alkyl group having 1 or more carbon atoms and 4 or less carbon atoms.

The constituting unit represented by formula 2 is a constituting unit which is derived by polymerizing an unsaturated monomer represented by formula 2' given below:

(formula 2')

wherein each of $R^4$, $X^1$, $Y^1$, $X^2$ and $R^5$ in formula 2' are the same as those defined in formula 2.

The preferred substituents in formula 2 and formula 2' are as follows.

—$Y^1$—$X^2$ is a group selected from an alkyl group having 1 or more carbon atoms and 18 or less carbon atoms, an isobornyl group, —$(CH_2)_p$—$N(R^5)_2$, —$(CH_2)_p$—$OR^5$, —$C(CH_3)_2$—$N(R^5)_2$, and —$C(CH_3)_2$—$OR^5$, where p is 1 or more and 3 or less, and $R^5$ is a hydrogen atom or an alkyl group having 1 or more carbon atoms and 4 or less carbon atoms;

$Y^1$ is a group containing 1 to 15 polyoxyalkylene groups having 2 or 3 carbon atoms;

$X^2$ is —$N(R^5)_2$ or —$OR^5$, wherein the alkyl group of $R^5$ includes a methyl group, an ethyl group, a propyl group, and a butyl group. Accordingly, specific examples where $X^2$ is —$N(R)_2$ include a dimethylamino group, a methylethylamino group, a diethylamino group, a dipropylamino group, a dibutylamino group, and the like. Further, specific examples where $X^2$ is —$OR^5$ include a methoxy group, an ethoxy group, a propoxy group, a butoxy group, and the like. Here, $R^5$ in $N(R^5)_2$ may be identical or different.

Specific examples of the unsaturated monomers represented by formula 2' include dimethylaminopropyl acrylamide, dimethylaminoethyl acrylate, dimethylaminoethyl methacrylate, diethylaminoethyl acrylate, diethylaminoethyl methacrylate, and the like, and dimethylaminopropyl acrylamide is preferred, from the viewpoint of enhancing hairwash removability and hydrolytic resistance.

<Constituting Unit Represented by Formula 3>

The constituting unit represented by formula 3 as used herein has the following structure:

(formula 3)

wherein $R^6$ is a hydrogen atom or a methyl group, and $X^3$ is an aromatic group having 6 or more carbon atoms and 12 or less carbon atoms.

The constituting unit represented by formula 3 is a constituting unit which is derived by polymerizing an unsaturated monomer represented by formula 3' given below.

(formula 3')

wherein each of $R^6$ and $X^3$ in formula 3' are the same as those defined in formula 3.

The preferred substituents in formula 3 and formula 3' are as follows.

$X^3$ is an aromatic group having the number of carbon atoms of 6 or more and 12 or less, and preferably 6 or more and 10 or less. $X^3$ includes a phenyl group, a tolyl group, a xylyl group, and the like.

The unsaturated monomers represented by formula 3' include styrene, α-methylstyrene, 4-methylstyrene, 4-butylstyrene, dimethylstyrene, and the like. Styrene is preferred, from the viewpoint of enhancing hygroscopic resistance.

The cosmetic composition of the present invention is exemplified by the following embodiments (Ia), (Ib), (IIa), and (IIb) with regard to the combinations of the polymers blended.

Embodiment of Ia

Ia is a cosmetic composition containing the following Components (A) and (B):

Component (A): a hydrophobic cationic polymer which dissolves in ethanol at 25° C. in an amount of 1% by mass or more, and has a glass transition temperature Tg of 30° C. or higher; and Component (B): a hydrophilic anionic polymer which dissolves in ethanol at 25° C. in an amount of 1% by mass or more.

In the above embodiment of Ia, from the viewpoint of maintaining styling and having hygroscopic resistance, it is preferable that Component (A) is a polymer containing a constituting unit derived from one or more members selected from acrylamide monomers having a linear alkyl group having 1 or more carbon atoms and 12 or less carbon atoms or a branched alkyl group having 3 or more carbon atoms and 12 or less carbon atoms and aromatic vinyl monomers, and a constituting unit derived from a monomer having an amino group; and Component (B) is a polymer containing a constituting unit derived from a monomer having a carboxy group.

Here, the phrase "derived from" as used herein shows that the unsaturated monomers are polymerized to form a polymer.

In the above embodiment of Ia, from the same viewpoint, it is more preferable that Component (A) is prepared so that the constituting units represented by formula 1a given below are contained in an amount of preferably 56% by mass or more, more preferably 60% by mass or more, and even more preferably 70% by mass or more, or the constituting units represented by formula 2a given below are contained in an amount of preferably 45% by mass or more, more preferably 50% by mass or more, and even more preferably 60% by mass or more, or the constituting units represented by formula 3 given below are contained in an amount of preferably 45% by mass or more, more preferably 50% by mass or more, and even more preferably 60% by mass or more, and it is more preferable that Component (B) is prepared so that a total of the constituting units represented by formula 1b given below, the constituting units represented by formula 2b given below, and the constituting units represented by formula 2c given below is contained in an amount of preferably 35% by mass or more, more preferably 40% by mass or more, and even more preferably 50% by mass or more.

Formula 1a:

(formula 1a)

wherein $R^1$ is a hydrogen atom or a methyl group; and each of $R^2$ and $R^3$ is independently a hydrogen atom or a hydrocarbon group having 1 or more carbon atoms and 12 or less carbon atoms which may have a substituent, with proviso that when either one of $R^2$ or $R^3$ is a hydrogen atom, the other is a hydrocarbon group having 4 or more carbon atoms and 12 or less carbon atoms, and when both $R^2$ and $R^3$ are not a hydrogen atom, they are hydrocarbon groups having a total number of carbon atoms of $R^2$ and $R^3$ of 5 or more and 24 or less; or alternatively, $R^2$ and $R^3$ may be bound to each other to form a ring structure, and a total number of carbon atoms of $R^2$ and $R^3$ in that case is 5 or more and 24 or less;

Formula 1b:

wherein $R^1$ is a hydrogen atom or a methyl group; and each of $R^2$ and $R^3$ is independently a hydrogen atom or a hydrocarbon group having 1 or more carbon atoms and 3 or less carbon atoms which may have a substituent, with proviso that when either one of $R^2$ or $R^3$ is a hydrogen atom, the other is a hydrocarbon group having 1 or more carbon atoms and 3 or less carbon atoms, and when both $R^2$ and $R^3$ are not a hydrogen atom, they are hydrocarbon groups having a total number of carbon atoms of $R^2$ and $R^3$ of 2 or more and 4 or less;

alternatively, $R^2$ and $R^3$ may be bound to each other to form a ring structure, and a total number of carbon atoms of $R^2$ and $R^3$ in that case is 3 or more and 4 or less.

Formula 2a:

(formula 2a)

wherein $R^4$ is a hydrogen atom or a methyl group, X is an oxygen atom, —$Y^1$—$X^2$ is an alkyl group having 1 or more carbon atoms and 18 or less carbon atoms or an isobornyl group;

Formula 2b:

(formula 2b)

wherein $R^4$ is a hydrogen atom or a methyl group, $X^1$ is an oxygen atom, $Y^1$ is a group containing 1 to 15 polyoxyalkylene groups having 2 or 3 carbon atoms, and —$X^2$ is a hydrogen atom, —$CH_3$, or —$C_2H_5$;

Formula 2c:

(formula 2c)

wherein $R^4$ is a hydrogen atom or a methyl group, $X^1$ is NH or an oxygen atom, $Y^1$ is an alkylene group having 1 or more carbon atoms and 3 or less carbon atoms or —C(CH$_3$)$_2$—, $X^2$ is —N(R$^5$)$_2$ or —OR$^5$, where $R^5$ is a hydrogen atom or an alkyl group having 1 or more carbon atoms and 4 or less carbon atoms;

Formula 3:

(formula 3)

wherein $R^6$ is a hydrogen atom or a methyl group, and $X^3$ is an aromatic group having 6 or more carbon atoms and 12 or less carbon atoms.

As the hydrophobic cationic polymer of Component (A) described above, for example, polymers in which styrenic monomers and DMAPAA monomers are polymerized and the like can be used.

As a commercially available product of the hydrophilic anionic polymer of Component (B), for example, Resyn 28-2930 manufactured by Akzo Nobel or the like can be used.

The cosmetic composition of the embodiment Ia described above is preferably combinations listed in Examples 1 to 7.

Embodiment of Ib

Ib is a cosmetic composition containing the following Components (A) and (B):
Component (A): a hydrophobic anionic polymer which dissolves in ethanol at 25° C. in an amount of 1% by mass or more, and has a glass transition temperature Tg of 30° C. or higher;
Component (B): a hydrophilic cationic polymer which dissolves in ethanol at 25° C. in an amount of 1% by mass or more.

In the above embodiment of Ib, it is preferable that Component (A) is a polymer containing a constituting unit derived from one or more members selected from acrylamide monomers having a linear alkyl group having 1 or more carbon atoms and 12 or less carbon atoms or a branched alkyl group having 3 or more carbon atoms and 12 or less carbon atoms and aromatic vinyl monomers, from the viewpoint of maintaining styling and having hygroscopic resistance; and
Component (B) is a polymer containing a constituting unit derived from a monomer having an amino group.

In the above embodiment of Ib, from the same viewpoint, it is more preferable that Component (A) is prepared so that the constituting units represented by formula 1a mentioned above are contained in an amount of preferably 60% by mass or more, more preferably 70% by mass or more, and even more preferably 80% by mass or more, or the constituting units represented by formula 2a mentioned above are contained in an amount of preferably 45% by mass or more, more preferably 50% by mass or more, and even more preferably 60% by mass or more, or the constituting units represented by formula 3 mentioned above are contained in an amount of preferably 45% by mass or more, more preferably 50% by mass or more, and even more preferably 60% by mass or more, and it is more preferable that Component (B) is prepared so that a total of the constituting units represented by formula 1b mentioned above, the constituting units represented by formula 2b mentioned above, and the constituting units represented by formula 2c mentioned above is contained in an amount of preferably 44% by mass or more, more preferably 50% by mass or more, and even more preferably 60% by mass or more.

As commercially available products of the hydrophobic anionic polymer of Component (A) described above, for example, Tilamar Fix A1000 manufactured by DSM, Ultrahold Strong manufactured by BASF, Plascize L-9909B manufactured by GOO CHEMICAL CO., LTD. or the like can be used.

As examples of the hydrophilic cationic polymer of Component (B) described above, a polymer described in Synthesis Example 1 of Japanese Patent Laid-Open No. Hei-08-291206 or the like can be used, and as a commercially available product, for example, HC Polymer 3A manufactured by Osaka Organic Chemical Industries, Ltd., Plascize L-514 manufactured by GOO CHEMICAL CO., LTD., or the like can be used.

Embodiment of IIa

IIa is a cosmetic composition containing the following Components (A) and (B):
Component (A): a hydrophobic nonionic polymer which dissolves in ethanol at 25° C. in an amount of 1% by mass or more, and has a glass transition temperature Tg of 30° C. or higher; and
Component (B): a hydrophilic cationic polymer which dissolves in ethanol at 25° C. in an amount of 1% by mass or more.

In the above embodiment of IIa, from the viewpoint of maintaining styling and having hygroscopic resistance, it is preferable that Component (A) is a nonionic polymer containing a constituting unit derived from one or more members selected from acrylamide monomers having a linear alkyl group having 1 or more carbon atoms and 12 or less carbon atoms or a branched alkyl group having 3 or more carbon atoms and 12 or less carbon atoms and aromatic vinyl monomers, and
Component (B) is a polymer containing a constituting unit derived from a monomer having an amino group.

In the above embodiment of IIa, from the same viewpoint, it is more preferable that Component (A) is prepared so that the constituting units represented by formula 1a mentioned above are contained in an amount of preferably 56% by mass or more, more preferably 60% by mass or more, and even more preferably 70% by mass or more, or the constituting units represented by formula 2a mentioned above are contained in an amount of preferably 45% by mass or more, more preferably 50% by mass or more, and even more preferably 60% by mass or more, or the constituting units represented by formula 3 mentioned above are contained in an amount of preferably 45% by mass or more, more preferably 50% by mass or more, and even more preferably 60% by mass or more, and it is more preferable that Component (B) is prepared so that a total of the constituting units represented by formula 1b mentioned above, the constituting units represented by formula 2b mentioned above, and the constituting units represented by formula 2c mentioned above is contained in an amount of preferably 44% by mass or more, more preferably 50% by mass or more, and even more preferably 60% by mass or more.

As a commercially available product of the hydrophobic nonionic polymer of Component (A) described above, for example, S-LEC BM-1 manufactured by SEKISUI CHEMICAL CO., LTD., or the like can be used.

As examples of the hydrophilic cationic polymer of Component (B) described above, a polymer described in Synthesis Example 1 of Japanese Patent Laid-Open No. Hei-08-291206 or the like can be used, and as an example of a commercially available product, HC Polymer 3A manufactured by Osaka Organic Chemical Industries, Ltd., or Plascize L-514 manufactured by GOO CHEMICAL CO., LTD. can be used.

As the cosmetic composition of the embodiment IIa described above, combinations given in Example 8 are preferred.

Embodiment of IIb

IIb is a cosmetic composition containing the following Components (A) and (B):
Component (A): a hydrophobic nonionic polymer which dissolves in ethanol at 25° C. in an amount of 1% by mass or more, and has a glass transition temperature Tg of 30° C. or higher; and
Component (B): a hydrophilic anionic polymer which dissolves in ethanol at 25° C. in an amount of 1% by mass or more.

In the above embodiment of IIb, from the viewpoint of maintaining styling and having hygroscopic resistance, it is preferable that Component (A) is a nonionic polymer containing a constituting unit derived from one or more members selected from acrylamide monomers having a linear alkyl group having 1 or more carbon atoms and 12 or less carbon atoms or a branched alkyl group having 3 or more carbon atoms and 12 or less carbon atoms and aromatic vinyl monomers, and
Component (B) is a polymer containing a constituting unit derived from a monomer having a carboxy group.

In the above embodiment of IIb, from the same viewpoint, it is more preferable that Component (A) is prepared so that the constituting units represented by formula 1a mentioned above are contained in an amount of preferably 56% by mass or more, more preferably 60% by mass or more, and even more preferably 70% by mass or more, or the constituting units represented by formula 2a mentioned above are contained in an amount of preferably 45% by mass or more, more preferably 50% by mass or more, and even more preferably 60% by mass or more, or the constituting units represented by formula 3 mentioned above are contained in an amount of preferably 45% by mass or more, more preferably 50% by mass or more, and even more preferably 60% by mass or more, and it is more preferable that Component (B) is prepared so that a total of the constituting units represented by formula 1b mentioned above, the constituting units represented by formula 2b mentioned above, and the constituting units represented by formula 2c mentioned above is contained in an amount of preferably 44% by mass or more, more preferably 50% by mass or more, and even more preferably 60% by mass or more.

As a commercially available product of the hydrophobic nonionic polymer of Component (A) described above, for example, S-LEC BM-1 manufactured by SEKISUI CHEMICAL CO., LTD., or the like can be used.

As a commercially available product of the hydrophilic anionic polymer of Component (B) described above, for example, Resyn 28-2930 manufactured by Akzo Nobel, or the like can be used.

[Other Optional Components]

The cosmetic composition of the present invention can optionally further contain various components used in ordinary hair cosmetics, including, for example, a cationic surfactant, an anionic surfactant, a nonionic surfactant, or an amphoteric surfactant, other than Components (A) and (B), a pH adjusting agent, vitamins, a protein, amino acids, crude medicines, an anticorrosive (a preservative), an ultraviolet absorbent, an antioxidant, a colorant or the like.

The cosmetic composition of the present invention may further contain a medium. The medium which is usable includes water; alcohols such as ethanol, isopropanol, and glycerol; and the like. These media may be used alone in a single kind or may be used in a mixture of two or more kinds. Among these media, ethanol is preferred, from the viewpoint of safety to human bodies. The amount of the medium in the cosmetic composition is preferably 4% by mass or more, more preferably 30% by mass or more, and even more preferably 50% by mass or more, and on the other hand, the amount is preferably 98.4% by mass or less, more preferably 98% by mass or less, and even more preferably 95% by mass or less.

The cosmetic composition of the present invention can be used in, for example, a cosmetic composition for hair, eyelashes, or the like. Among them, it is preferable to use the cosmetic composition as a hair cosmetic composition. The present invention also provides a method of hair styling, including applying a cosmetic composition of the present invention to hairs.

[Cosmetics]

The cosmetic composition of the present invention is preferably used as cosmetics such as hair styling agents and hair conditioning agents.

With respect to the above-mentioned embodiments, the present invention further discloses cosmetic compositions and a method of hair styling given below.

<1> A cosmetic composition containing the following Components (A) and (B):
Component (A): a hydrophobic polymer which dissolves in ethanol at 25° C. in an amount of 1% by mass or more, and has a glass transition temperature Tg of 30° C. or higher, the polymer having a different kind of an electric charge as the following Component (B), or not having an electric charge; and
Component (B): a hydrophilic ionic polymer which dissolves in ethanol at 25° C. in an amount of 1% by mass or more.

<2> The cosmetic composition according to the above <1>, wherein Component (A) is a cationic polymer or a nonionic polymer, and Component (B) is an anionic polymer.

<3> The cosmetic composition according to the above <1>, wherein Component (A) is an anionic polymer or a nonionic polymer, and Component (B) is a cationic polymer.

<4> The cosmetic composition according to any one of the above <1> to <3>, wherein the weight-average molecular weight of Component (A) is 5000 or more and 500000 or less.

<5> The cosmetic composition according to any one of the above <1> to <4>, wherein the weight-average molecular weight of Component (A) is more preferably 20000 or more and 450000 or less, and even more preferably 100000 or more and 350000 or less.

<6> The cosmetic composition according to any one of the above <1> to <5>, wherein Component (A) and/or (B) has one or more groups selected from alkylamide groups and aminoalkylamide groups.

<7> The cosmetic composition according to any one of the above <1> to <6>, wherein Component (A) and/or (B) has one or more constituting units selected from formula 1, formula 2, and formula 3 given below:

Formula 1:

(formula 1)

wherein $R^1$ is a hydrogen atom or a methyl group; and each of $R^2$ and $R^3$ is independently a hydrogen atom or a hydrocarbon group having 1 or more carbon atoms and 12 or less carbon atoms which may have a substituent, with proviso that when either one of $R^2$ or $R^3$ is a hydrogen atom, the other is a hydrocarbon group having 1 or more carbon atoms and 12 or less carbon atoms, and when both $R^2$ and $R^3$ are not a hydrogen atom, they are hydrocarbon groups having a total number of carbon atoms of $R^2$ and $R^3$ of 2 or more and 24 or less;

alternatively, $R^2$ and $R^3$ may be bound to each other to form a ring structure, and a total number of carbon atoms of $R^2$ and $R^3$ in that case is 3 or more and 24 or less;

Formula 2:

(formula 2)

wherein $R^4$ is a hydrogen atom or a methyl group;

if $X^1$ is an oxygen atom,

—$Y^1$—$X^2$ is a group selected from an alkyl group having 1 or more carbon atoms and 18 or less carbon atoms, an isobornyl group, —$(CH_2)_p$—$N(R^5)_2$, —$(CH_2)_p$—$OR^5$, —$C(CH_3)_2$—$N(R^5)_2$, and —$C(CH_3)_2$—$OR^5$, where p is 1 or more and 3 or less, and $R^5$ is a hydrogen atom or an alkyl group having 1 or more carbon atoms and 4 or less carbon atoms;

alternatively, $Y^1$ is a group containing 1 to 15 polyoxyalkylene groups having 2 or 3 carbon atoms, $X^2$ is a hydrogen atom, —$CH_3$, or —$C_2H_5$, or if $X^1$ is NH, $Y^1$ is an alkylene group having 1 or more carbon atoms and 3 or less carbon atoms, $X^2$ is —$N(R^5)_2$, where $R^5$ is a hydrogen atom or an alkyl group having 1 or more carbon atoms and 4 or less carbon atoms; and Formula 3:

(formula 3)

wherein $R^6$ is a hydrogen atom or a methyl group, and $X^3$ is an aromatic group having 6 or more carbon atoms and 12 or less carbon atoms.

<8> The cosmetic composition according to any one of the above <1> to <7>, wherein Component (A)/Component (B) is 0.1 or more and 5.0 or less.

<9> The cosmetic composition according to any one of the above <1> to <8>, wherein Component (A)/Component (B) is more preferably 0.5 or more and 3.0 or less, and even more preferably 0.8 or more and 1.5 or less.

<10> The cosmetic composition according to any one of the above <1> to <9>, wherein in Component (A) the amount of the amine is 1% by mass or more and 60% by mass or less, or the amount of the carboxylic acid is 1% by mass or more and 50% by mass or less.

<11> The cosmetic composition according to any one of the above <1> to <10>, wherein the amount of the amine in a case where Component (A) is a cationic polymer is more preferably 3% by mass or more and 45% by mass or less, and even more preferably 5% by mass or more and 35% by mass or less.

<12> The cosmetic composition according to any one of the above <1> to <10>, wherein the amount of the carboxylic acid in a case where Component (A) is an anionic polymer is more preferably 3% by mass or more and 35% by mass or less, even more preferably 5% by mass or more and 30% by mass or less, and still even more preferably 5% by mass or more and 20% by mass or less.

<13> The cosmetic composition according to any one of the above <1> to <12>, wherein in Component (B) the amount of the amine is 1% by mass or more and 60% by mass or less, or the amount of the carboxylic acid is 1% by mass or more and 50% by mass or less.

<14> The cosmetic composition according to any one of the above <1> to <13>, wherein the amount of the amine in a case where Component (B) is a cationic polymer is more preferably 3% by mass or more and 45% by mass or less, and even more preferably 5% by mass or more and 35% by mass or less.

<15> The cosmetic composition according to any one of the above <1> to <13>, wherein the amount of the carboxylic acid in a case where Component (B) is an anionic polymer is more preferably 3% by mass or more and 35% by mass or less, even more preferably 5% by mass or more and 30% by mass or less, and still even more preferably 5% by mass or more and 20% by mass or less.

<16> The cosmetic composition according to any one of the above <1> to <15>, wherein the cosmetic composition further contains one or more media selected from the group consisting of water, ethanol, isopropanol, and glycerol, wherein the amount of the medium in the cosmetic composition is preferably 4% by mass or more and 98.4% by mass or less, more preferably 30% by mass or more and 98% by mass or less, and even more preferably 50% by mass or more and 95% by mass or less.

<17> The cosmetic composition according to any one of the above <1> to <16>, wherein ethanol is used as the medium.

<18> The cosmetic composition according to any one of the above <1> to <17>, for use in hair.

<19> The cosmetic composition according to any one of the above <1> to <18>, wherein the glass transition point Tg of Component (A) is preferably 30° C. or higher and 180° C. or lower, more preferably 40° C. or higher and 150° C. or lower, even more preferably 50° C. or higher and 130° C. or lower, still even more preferably 60° C. or higher and 130° C. or lower, and still even more preferably 70° C. or higher and 130° C. or lower.

<20> The cosmetic composition according to any one of the above <1> to <19>, wherein the content of Component (A) is preferably 9% by mass or more and 83% by mass or less, more preferably 33% by mass or more and 75% by mass or less, and even more preferably 44% by mass or more and 60% by mass or less.

<21> The cosmetic composition according to any one of the above <1> to <20>, wherein the glass transition point Tg of Component (B) is preferably 0° C. or higher and 130° C. or lower, more preferably 10° C. or higher and 120° C. or lower, even more preferably 25° C. or higher and 100° C. or lower, and still even more preferably 40° C. or higher and 100° C. or lower.

<22> The cosmetic composition according to any one of the above <1> to <21>, wherein the weight-average molecular weight of Component (B) is preferably 5000 or more and 500000 or less, more preferably 20000 or more and 450000 or less, and even more preferably 100000 or more and 350000 or less.

<23> The cosmetic composition according to any one of the above <1> to <22>, wherein the content of Component (B) is preferably 17% by mass or more and 91% by mass or less, more preferably 25% by mass or more and 67% by mass or less, and even more preferably 40% by mass or more and 56% by mass or less.

<24> The cosmetic composition according to any one of the above <1> to <23>, wherein the cosmetic composition contains the following Components (A) and (B):
Component (A): a hydrophobic cationic polymer which dissolves in ethanol at 25° C. in an amount of 1% by mass or more, and has a glass transition temperature Tg of 30° C. or higher; and
Component (B): a hydrophilic anionic polymer which dissolves in ethanol at 25° C. in an amount of 1% by mass or more.

<25> The cosmetic composition according to any one of the above <1> to <23>, wherein the cosmetic composition contains the following Components (A) and (B):
Component (A): a hydrophobic anionic polymer which dissolves in ethanol at 25° C. in an amount of 1% by mass or more, and has a glass transition temperature Tg of 30° C. or higher; and
Component (B): a hydrophilic cationic polymer which dissolves in ethanol at 25° C. in an amount of 1% by mass or more.

<26> The cosmetic composition according to any one of the above <1> to <23>, wherein the cosmetic composition contains the following Components (A) and (B):
Component (A): a hydrophobic nonionic polymer which dissolves in ethanol at 25° C. in an amount of 1% by mass or more, and has a glass transition temperature Tg of 30° C. or higher; and
Component (B): a hydrophilic cationic polymer which dissolves in ethanol at 25° C. in an amount of 1% by mass or more.

<27> The cosmetic composition according to any one of the above <1> to <23>, wherein the cosmetic composition contains the following Components (A) and (B):
Component (A): a hydrophobic nonionic polymer which dissolves in ethanol at 25° C. in an amount of 1% by mass or more, and has a glass transition temperature Tg of 30° C. or higher; and
Component (B): a hydrophilic anionic polymer which dissolves in ethanol at 25° C. in an amount of 1% by mass or more.

<28> A method of styling hair, including applying a cosmetic composition as defined in any one of the above <1> to <27> to hair.

EXAMPLES

The present invention will be described more specifically by means of the following Examples and the like. Here, the Examples and the like are mere exemplifications of the present invention, without intending to limit the present invention thereto. Parts in Examples are parts by mass unless specified otherwise. Here, "ambient pressure" means 101.3 kPa, and "room temperature" means 25° C.

<Measurement of Weight-Average Molecular Weight Mw>

A weight-average molecular weight Mw was obtained by gel permeation chromatography (GPC) under the following conditions. Here, the eluent in the measurement of an anionic polymer was a solution of 60 mM phosphoric acid and 50 mM lithium bromide in N,N-dimethylformamide.

<Measurement Conditions for GPC>
Columns: two columns of "α-M," manufactured by Tosoh Corporation being connected in a series upon use;
an eluent: 50 mM lithium bromide in an N,N-dimethylformamide solution;
a flow rate: 1.0 m/min;
a column temperature: 40° C.;
a detector: RI;
a sample: 5 mg/mL N,N-dimethylformamide solution, 100 μL; and
a calibration curve: molecular weights of polystyrenes: 8420000, 1090000, and 96400 manufactured by Tosoh Corporation, molecular weight of polystyrene: 30000 manufactured by Nishio Kogyo Kabushiki Kaisha, and molecular weights of polystyrenes: 5400 and 500 manufactured by Tosoh Corporation.

<Glass Transition Temperature>

The glass transition temperatures for the polymers synthesized in the present application were calculated using the FOX formula in accordance with the initially charged compositional ratio. The glass transition temperatures of commercially available polymers were measured with differential scanning colorimetry (DSC) under the following conditions. The FOX formula is a relational formula of a glass transition temperature (Tg) of a copolymer and a glass transition temperature (Tgi) of a homopolymer in which each of the monomers constituting the copolymer is homopolymerized, as represented by the following formula:

$$1/Tg = \sum (Wi/Tgi)$$

wherein Tg: a glass transition temperature (K) of a copolymer;
Tgi: a glass transition temperature (K) of a homopolymer of a monomer i; and Wi: a weight percentage of the monomer i in the copolymer.

Measurement apparatus: DSC 7020, manufactured by Hitachi High-Tech Science Corporation;

Temperature profiles: A glass transition temperature was obtained from 2nd heating under the following temperature profiles:

1st heating: heating from 25° C. to 150° C. at a rate of 50° C./min, and holding thereat for 10 minutes, 1st cooling: cooling from 150° C. to 25° C. at a rate of 10° C./min, and holding thereat for 10 minutes, 2nd heating: heating from 25° C. to 150'C at a rate of 10° C./min, and holding thereat for 10 minutes, and 2nd cooling: cooling from 150° C. to 25° C. at a rate of 10° C./min, and holding thereat for 10 minutes.

<Amount of Amine in Commercially Available Product>

The amount of the amine was calculated from an areal ratio of peaks with the internal standard in accordance with NMR measurement.

Solvent: Chloroform-d, manufactured by FUJIFILM Wako Pure Chemical Corporation;

Integration count: 32 times;

Relaxation time: 10 seconds; and

Internal standard: p-Dinitrobenzene manufactured by FUJIFILM Wako Pure Chemical Corporation.

<Amount of Carboxylic Acid in Commercially Available Product>

A 10 g sample was taken, 30 mL of a mixed solvent (remark 1) was added thereto, the mixture was heated to dissolve, and a mixed solution was titrated with a 0.1 mol/L potassium hydroxide ethanol solution (remark 2), while occasionally shaking and mixing the solution. The endpoint of the titration was defined as a point where a pale red color of the solution was continued for 30 seconds (indicator: several drops of a phenolphthalein solution (remark 3)). An empty test was carried out in the same manner, and compensated therewith.

$$\text{Acid value} = a \times 5.611/b$$

a: An amount of a 0.1 mol/L potassium hydroxide ethanol solution consumed, mL; and b: An amount of the sample, g.

(remark 1) Mixed solvent: Several drops of a phenolphthalein solution (remark 3) was added as an indicator to a toluene/ethanol liquid mixture (2:1), both manufactured by FUJIFILM Wako Pure Chemical Corporation. Immediately before use the liquid mixture was neutralized with a 0.1 mol/L potassium hydroxide ethanol solution (remark 2) until the colors changed to a faintly red color.

(remark 2) A 0.1 mol/L potassium hydroxide ethanol solution: manufactured by KATAYAMA CHEMICAL, LTD., or an equivalent commercially available product.

(remark 3) Phenolphthalein solution: One gram of Phenolphthalein manufactured by FUJIFILM Wako Pure Chemical Corporation was dissolved in 90 mL of ethanol and 10 mL of water.

<Measurement of Amount of Polymer Dissolved in Ethanol>

The measurement of the amount of the polymer dissolved in ethanol as used herein was carried out as follows.

A polymer was added to 1 L of ethanol at 25° C. so as to have a concentration of 1% by mass, the mixture was stirred at 50 rpm for 3 minutes, and the mixture was then filtered with a No. 2 filter paper. It was judged that the polymer dissolves in an amount of 1% by mass or more in ethanol at 25° C., if insoluble remnants do not remain on the filter paper in an amount of 0.1 g or more.

Preparation of Polymers a1, a3, and b1 to b3

A four-neck flask equipped with a reflux condenser, a liquid pumping device, a thermometer, a nitrogen gas inlet tube, and an agitating device was heated with an oil bath at 50° C. The monomers of which constituting ratios were shown in Table 1-A were dissolved in 75 to 100 parts by mass of ethanol (213 parts by mass of ethanol, only for a3) so as to contain 100 parts by mass of the monomers. In addition, 0.2 mol % of an initiator V-65B was dissolved in the monomer solution so as to have a concentration of 5% by mass based on the monomers. The above monomer solution and the initiator solution were added dropwise concurrently to the flask over 130 minutes under a nitrogen atmosphere, and the mixture was kept at 50° C. for 130 minutes, and further held at 80° C. for 120 minutes, to carry out the reaction. After the polymerization, the ethanol solution of the polymer was poured in n-hexane to allow reprecipitation and purification, and the product was vacuum-dried at 80° C.

Preparation of Polymers a2

A four-neck flask equipped with a reflux condenser, a dropping funnel, a thermometer, a nitrogen gas inlet tube, and an agitating device was heated with an oil bath at 75° C. One hundred parts by mass of the monomers of which constituting ratios were shown in Table 1-A, and an initiator AIBN in an amount of 0.2 mol % based on the monomers were dissolved in 43 to 67 parts by mass of toluene. The above solution was added dropwise to the flask over 2 hours under a nitrogen atmosphere, and further held at 75° C. for 2 to 4 hours, to carry out the reaction. After the polymerization, the toluene solution of the polymer was poured in n-hexane to allow reprecipitation and purification, and the product was vacuum-dried at 80° C.

Polymer a4

Tilamar Fix A1000 manufactured by DSM, Mw: 120000, and Tg: 98° to 108° C. was used.

Polymer a5

Polybutyl acrylate manufactured by Sigma-Aldrich, Mw: 60000, and Tg: −49° C. was used.

Polymer b4

Plascize L-514 manufactured by GOO CHEMICAL CO., LTD. was used.

Preparation of Polymer b5

A four-neck flask equipped with a reflux condenser, a liquid pumping device, a thermometer, a nitrogen gas inlet tube, and an agitating device was heated with an oil bath at 83° C. The monomers of which constituting ratios were shown in Table 1-A were dissolved in 226 parts by mass of ethanol so as to contain 100 parts by mass of the monomers. In addition, 0.2 mol % of an initiator V-65B was dissolved in the ethanol solution so as to have a concentration of 7% by mass based on the monomers. The above monomer solution and the initiator solution were added dropwise concurrently to the flask over 130 minutes under a nitrogen atmosphere, to carry out the reaction. After the polymerization, the ethanol solution of the polymer was poured in n-hexane to allow reprecipitation and purification, and the product was vacuum-dried at 80° C.

TABLE 1-A

|  | TBAA, % by Mass | St, % by Mass | DMPAA, % by Mass | PEGMA, % by Mass | DMAA, % by Mass | EA, % by Mass | AA, % by Mass | DMAEMA, % by Mass | Mw | Tg °C. |
|---|---|---|---|---|---|---|---|---|---|---|
| Polymer a1 | 70 | 0 | 5 | 10 | 15 | 0 | 0 | 0 | 190,000 | 95 |
| Polymer a2 | 0 | 45 | 0 | 0 | 50 | 0 | 0 | 5 | 114,000 | 108 |
| Polymer a3 | 97 | 0 | 0 | 0 | 0 | 0 | 3 | 0 | 100,000 | 134 |
| Polymer b1 | 59.8 | 0 | 0 | 10.9 | 0 | 21.8 | 7.5 | 0 | 240,000 | 58 |
| Polymer b2 | 55 | 0 | 15 | 10 | 0 | 20 | 0 | 0 | 250,000 | 61 |
| Polymer b3 | 55 | 0 | 2 | 20 | 23 | 0 | 0 | 0 | 250,000 | 61 |
| Polymer b5 | 20 | 0 | 0 | 0 | 80 | 0 | 0 | 0 | 20,000 | 122 |

Here, it was confirmed that as to the transmittance of Polymers a1 to a4 and b1 to b4 mentioned above, all of a1 to a4 were less than 80%, and that all of b1 to b4 were 80% or more.

Further, it was confirmed that the amount of Polymers a1 to a5 and b1 to b5 mentioned above dissolved in ethanol at 25° C. all exceeded 1% by mass. Also, Table 1-B shows the visual observation results of the external appearances of a 1% by mass ethanol solution at 25° C. This ethanol solution is a cosmetic composition, where ethanol is a medium. Here, in Table 1-B, N means nonionic, A means anionic, and C means cationic.

TABLE 1-B

|  | External appearance of 1% by mass ethanol solution at 25° C. | Electric charger |
|---|---|---|
| Polymer a1 | Transparent | C |
| Polymer a2 | Transparent | C |
| Polymer a3 | Transparent | A |
| Polymer a4 | Transparent | A |
| Polymer a5 | Transparent | N |
| Polymer b1 | Transparent | A |
| Polymer b2 | Transparent | C |
| Polymer b3 | Transparent | C |
| Polymer b4 | Transparent | C |
| Polymer b5 | Transparent | N |

The details of the raw materials shown in Table 1-A are as follows.

TBAA: N-tert-Butylacrylamide, manufactured by MCC Unitec K.K.
St: Styrene, manufactured by FUJIFILM Wako Pure Chemical Corporation
DMPAA: N,N-Dimethylaminopropyl acrylamide, manufactured by KJ Chemicals Corporation
PEGMA: Polyethylene glycol monomethacrylate, manufactured by Shin-Nakamura Chemical Co., Ltd.
DMAA: Dimethylacrylamide, manufactured by KJ Chemicals Corporation
EA: Ethyl acrylate, manufactured by FUJIFILM Wako Pure Chemical Corporation
AA: Acrylic acid, manufactured by FUJIFILM Wako Pure Chemical Corporation
DMAEMA: 2-(Dimethylamino)ethyl methacrylate, manufactured by FUJIFILM Wako Pure Chemical Corporation
V-65B: 2,2'-Azobis-(2,4-dimethylvaleronitrile), manufactured by FUJIFILM Wako Pure Chemical Corporation
Ethanol: manufactured by FUJIFILM Wako Pure Chemical Corporation
n-Hexane: manufactured by FUJIFILM Wako Pure Chemical Corporation Example 1

Ethanol was added to Polymer a1, to provide a composition containing Component (A). The amount of ethanol at this time is an amount necessary to adjust its concentration to 10% by mass.

Ethanol was added to Polymer b1, and 2-amino-2-methyl-1-propanol manufactured by FUJIFILM Wako Pure Chemical Corporation was added thereto in an amount of 90 mol % based on the amount of the carboxylic acid of Polymer b1, to provide a composition containing Component (B). The amount of ethanol at this time is an amount necessary to adjust its concentration to 10% by mass.

To ethanol were added a composition containing Component (A), and a composition containing Component (B) to be included in amounts as listed in Table 2, and the mixture was homogeneously stirred, to provide a composition containing Components (A) and (B). The amount of ethanol at this time is an amount necessary to adjust its concentration to 5% by mass.

Ethanol was further added to a composition containing Components (A) and (B) so as to have a concentration of 0.5% by mass, to provide a cosmetic composition.

Examples 2 to 10 and Comparative Examples 1 to 3

The same procedures as in Example 1 were carried out except that each of the polymers listed in Tables 2 to 4 was used, to provide each of cosmetic compositions. Here, lactic acid was added in an amount of 90 mol % based on the amount of the amine, for the preparation of Component (B) in Example 9, in place of the addition of 2-amino-2-methyl-1-propanol manufactured by FUJIFILM Wako Pure Chemical Corporation in an amount of 90 mol % based on the amount of the carboxylic acid; and 2-amino-2-methyl-1-propanol and lactic acid were not added, for the preparation of the polymer of Example 10.

<Evaluation of Hygroscopic Resistance>
(a) Preparation of Hair Bundles for Evaluation Caucasian hair bundles having a length of 27.5 cm, a hair bundle width at root of hairs of 10 mm, and a total mass of 1.0 g were used for the evaluation. The hair bundles were previously washed with plain shampoo and plain rinse, and the hair bundles with hairs in a wet state were wound around a glass rod having a diameter of 20 mm and a length of 60 mm and fixed. The hair bundles were dried at 60° C. for one hour, and the hair bundles were then allowed to cool at room temperature for 15 minutes or more.

(Plain shampoo: EMAL 227, manufactured by Kao Corporation: 47.2% by mass, AMINON C-11S, manufactured by Kao Corporation: 2.50% by mass, sodium benzoate, manufactured by FUJIFILM Wako Pure Chemical Corporation: 1.10% by mass, sodium chloride, manufactured by FUJIFILM Wako Pure Chemical Corporation: 1.20% by mass, ion-exchanged water: 86.6% by mass)

(Plain rinse: QUARTAMIN E-80K, manufactured by Kao Corporation: 2.22% by mass, KALCOL, manufactured by Kao Corporation: 1.78% by mass, Propylene glycol, manufactured by FUJIFILM Wako Pure Chemical Corporation: 1.00% by mass, Phenoxyethanol, manufactured by FUJIFILM Wako Pure Chemical Corporation: 0.30% by mass, ion-exchanged water: 94.7% by mass)

A hair cosmetic (concentration: 0.5% by mass) in a state fixed to the glass rod in an amount 0.7 g was evenly applied to hair. The hair was again dried at 60° C. for one hour, and then allowed to cool at room temperature for 15 minutes or longer, and the hair bundles were removed from the glass rod, to provide hair bundles for evaluation.

(b) Apparatus and Method

Figure 1:
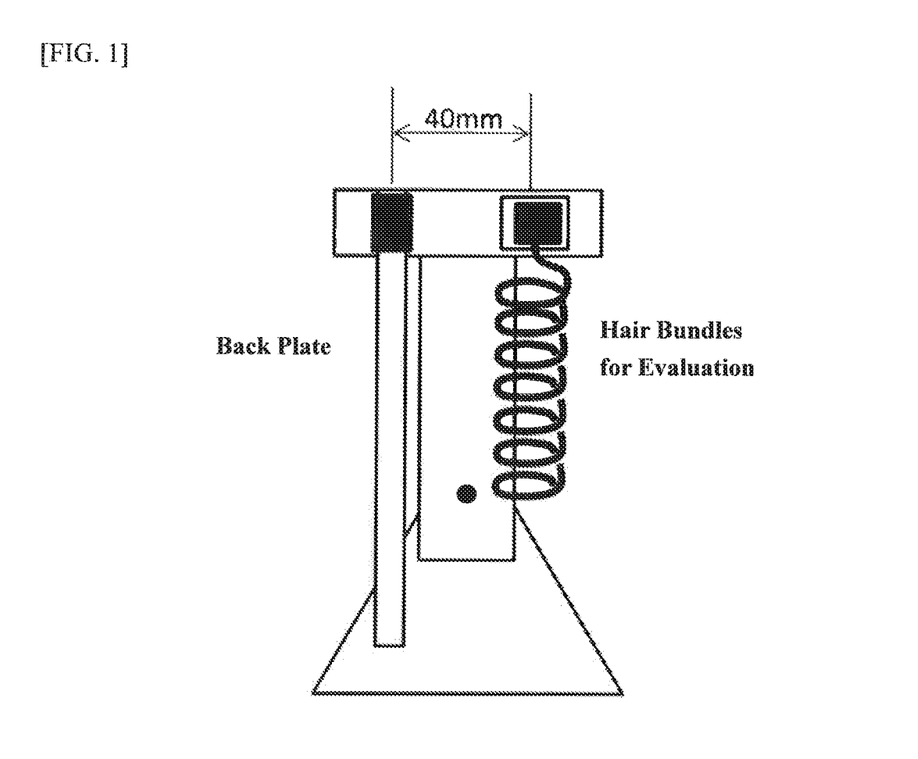
FIG. 1 is a front view showing a schematic constitution of a shaking apparatus used in the evaluation of the setting properties.
Figure 2:
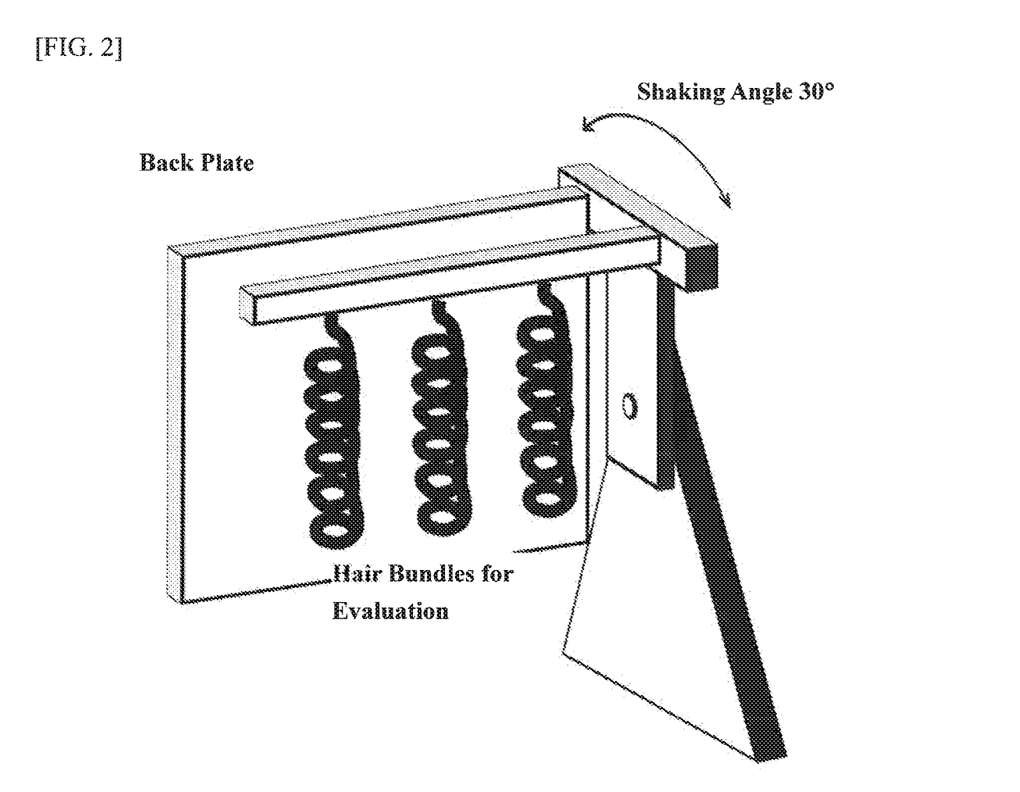
FIG. 2 is a perspective view showing a schematic constitution of a shaking apparatus used in the evaluation of the setting properties.

The hair setting properties were evaluated with a shaking apparatus shown in FIGS. 1 and 2. This shaking apparatus is an apparatus for shaking hair bundles that are partly fixed by oscillating rotary motions. With a distance from a center to an end of the rotating member of 120 mm, and a rotation angle of 30°, oscillating motions were repeated 90 times per minute. One end of hair bundles and a back plate of 5 mm in thickness were fixed to the rotating member at an interval of 40 mm, and impacts were given to the hair bundles by hitting the hair bundles that were swung due to shaking against the back plate. By using this apparatus, the hair bundles were shaken at 25° C. and 90% RH for 30 minutes. The length of the hair bundles after 30 minutes of shaking was measured, and a curl setting ratio was calculated in accordance with the following formula. The results are shown in Tables 2 to 4.

Curl Setting Ratio, % = {1 − (Length of Hair Bundles)/(Length of Untreated Hair Bundles = 27.5 cm)} × 100

TABLE 2

| | | Examples | | | | | | | |
|---|---|---|---|---|---|---|---|---|---|
| | | 1 | 2 | 3 | 4 | 5 | 6 | 7 | 8 |
| A | Polymer a1, g | 1.17 | 2.33 | 3 | 3.5 | 3.89 | 4.2 | 5.25 | 0 |
| | Polymer a2, g | 0 | 0 | 0 | 0 | 0 | 0 | 0 | 2.5 |
| | Tg of Component (A), ° C. | 96 | 96 | 96 | 96 | 96 | 96 | 96 | 108 |
| | Mw of Component (A) | 190,000 | 190,000 | 190,000 | 190,000 | 190,000 | 190,000 | 190,000 | 114,000 |
| | Amount of amine of Component (A), % by mass | 5 | 5 | 5 | 5 | 5 | 5 | 5 | 5 |
| | Amount of carboxylic acid of Component (A), % by mass | 0 | 0 | 0 | 0 | 0 | 0 | 0 | 0 |
| B | Polymer b1, g | 5.83 | 4.67 | 4 | 3.5 | 3.11 | 2.8 | 1.75 | 2.5 |
| | Amount of amine of Component (B), % by mass | 0 | 0 | 0 | 0 | 0 | 0 | 0 | 0 |
| | Amount of carboxylic acid of Component (B), % by mass | 7.5 | 7.5 | 7.5 | 7.5 | 7.5 | 7.5 | 7.5 | 7.5 |
| | A/B Mass ratio | 0.2 | 0.5 | 0.8 | 1 | 1.3 | 1.5 | 3 | 1 |
| | Curl setting ratio, % | 31 | 31 | 36 | 36 | 34 | 32 | 30 | 31 |

TABLE 3

|   |   | Ex. | |
|---|---|---|---|
|   |   | 9 | 10 |
| A | Polymer a3, g | 3.67 | 0 |
|   | Polymer a4, g | 0 | 2.5 |
|   | Tg of Component (A), °C. | 134 | 98-108 |
|   | Mw of Component (A) | 100,000 | 120,000 |
|   | Amount of amine of Component (A), % by mass | 0 | 0 |
|   | Amount of carboxylic acid of Component (A), % by mass | 3 | 19 |
| B | Polymer b2, g | 2.46 | 0 |
|   | Polymer b3, g | 0.88 | 0 |
|   | Polymer b4, g | 0 | 2.5 |
|   | Amount of amine of Component (B), % by mass | 12 | 7 |
|   | Amount of carboxylic acid of Component (B), % by mass | 0 | 0 |
|   | A/B Mass ratio | 1.1 | 1 |
|   | Curl setting ratio, % | 38 | 31 |

TABLE 4

|   |   | Comp. Ex. | | |
|---|---|---|---|---|
|   |   | 1 | 2 | 3 |
| A | Polymer a1, g | 0 | 0 | 3 |
|   | Polymer a5, g | 0 | 3 | 0 |
|   | Tg of Component (A), °C. | — | −54 | 96 |
|   | Mw of Component (A) | — | 60,000 | 190,000 |
|   | Amount of amine of Component (A), % by mass | — | 0 | 5 |
|   | Amount of carboxylic acid of Component (A), % by mass | — | 0 | 0 |
| B | Polymer b2, g | 0 | 2.95 | 0 |
|   | Polymer b3, g | 7 | 1.05 | 0 |
|   | Polymer b5, g | 0 | 0 | 4 |
|   | Amount of amine of Component (B), % by mass | 2 | 12 | 0 |
|   | Amount of carboxylic acid of Component (B), % by mass | 0 | 0 | 0 |
|   | A/B Mass ratio | 0 | 0.75 | 0.75 |
|   | Curl setting ratio, % | 16 | 9 | 7 |

As shown in Tables 2 and 3, it can be seen that all of the cosmetic compositions of the present invention are excellent in hygroscopic resistance. Here, Table 2 shows examples where Component (A) is a cationic polymer, and Component (B) is an anionic polymer, and Table 3 shows examples where Component (A) is an anionic polymer, and Component (B) is a cationic polymer. As shown in Table 4, it can be seen that all the comparative products that do not meet the requirements of the present invention are disadvantageous in hygroscopic resistance, as compared to the cosmetic compositions of the present invention.

INDUSTRIAL APPLICABILITY

The cosmetic composition of the present invention can be suitably used in cosmetics for hair.

The invention claimed is:

1. A cosmetic composition comprising the following Components (A) and (B):

Component (A): a hydrophobic cationic polymer which dissolves in ethanol at 25° C. in an amount of 1% by mass or more, has a glass transition temperature Tg of 30° C.-180° C., and is a polymer comprising a constituting unit derived from one or more members selected from acrylamide monomers having a linear alkyl group having 1 or more carbon atoms and 12 or less carbon atoms or a branched alkyl group having 3 or more carbon atoms and 12 or less carbon atoms and aromatic vinyl monomers, and a constituting unit derived from a monomer having an amino group, wherein Component (A) comprises constituting units represented by formula 1a in an amount of 56% by mass or more, or comprises constituting units represented by formula 2a in an amount of 45% by mass or more, or comprises constituting units represented by formula 3 in an amount of 45% by mass or more;

Component (B): a hydrophilic anionic polymer which dissolves in ethanol at 25° C. in an amount of 1% by mass or more, has a glass transition temperature Tg of 40° C.-130° C., and is a polymer comprising a constituting unit derived from a monomer having a carboxy group, wherein Component (B) comprises 35% by mass or more of a total of constituting units represented by formula 1b, constituting units represented by formula 2b, and constituting units represented by formula 2c, and wherein a mass ratio of Component (A) to Component (B) is 0.1 or more and 5.0 or less;

formula 1a:

(formula 1a)

wherein $R^1$ is a hydrogen atom or a methyl group; and each of $R^2$ and $R^3$ is independently a hydrogen atom or a hydrocarbon group having 1 or more carbon atoms and 12 or less carbon atoms which may have a substituent, with the proviso that:

when either one of $R^2$ or $R^3$ is a hydrogen atom, the other is a hydrocarbon group having 4 or more carbon atoms and 12 or less carbon atoms, and when both $R^2$ and $R^3$ are not a hydrogen atom, they are hydrocarbon groups having a total number of carbon atoms of $R^2$ and $R^3$ of 5 or more and 24 or less; or alternatively, $R^2$ and $R^3$ may be bound to each other to form a ring structure, and a total number of carbon atoms of $R^2$ and $R^3$ in that case is 5 or more and 24 or less;

formula 1b:

(formula 1b)

wherein $R^1$ is a hydrogen atom or a methyl group; and each of $R^2$ and $R^3$ is independently a hydrogen atom or a hydrocarbon group having 1 or more carbon atoms and 3 or less carbon atoms which may have a substituent, with the proviso that:

when either one of $R^2$ or $R^3$ is a hydrogen atom, the other is a hydrocarbon group having 1 or more carbon atoms and 3 or less carbon atoms, and when both $R^2$ and $R^3$ are not a hydrogen atom, they are hydrocarbon groups having a total number of carbon atoms of $R^2$ and $R^3$ of 2 or more and 4 or less; or alternatively, $R^2$ and $R^3$ may be bound to each other to form a ring structure, and a total number of carbon atoms of $R^2$ and $R^3$ in that case is 3 or more and 4 or less, formula 2a:

(formula 2a)

wherein $R^4$ is a hydrogen atom or a methyl group, $X^1$ is an oxygen atom, $—Y^1—X^2$ is an alkyl group having 1 or more carbon atoms and 18 or less carbon atoms or an isobornyl group;

formula 2b:

(formula 2b)

wherein $R^4$ is a hydrogen atom or a methyl group, $X^1$ is an oxygen atom, $Y^1$ is a group comprising 1 to 15 polyoxyalkylene groups having 2 or 3 carbon atoms, and $—X^2$ is a hydrogen atom, $—CH_3$, or $—C_2H_5$;

formula 2c:

(formula 2c)

wherein $R^4$ is a hydrogen atom or a methyl group, $X^1$ is NH or an oxygen atom, $Y^1$ is an alkylene group having 1 or more carbon atoms and 3 or less carbon atoms, or $—C(CH_3)_2—$, $X^2$ is $—N(R^5)_2$ or $—OR_5$, where $R^5$ is a hydrogen atom or an alkyl group having 1 or more carbon atoms and 4 or less carbon atoms;

formula 3:

(formula 3)

wherein $R^6$ is a hydrogen atom or a methyl group, and $X^3$ is an aromatic group having 6 or more carbon atoms and 12 or less carbon atoms.

2. The cosmetic composition according to claim 1, wherein Component (A) comprises constituting units represented by formula 1a in an amount of 56% by mass or more.

3. The cosmetic composition according to claim 1, wherein Component (A) comprises constituting units represented by formula 2a in an amount of 45% by mass or more.

4. The cosmetic composition according to claim 1, wherein Component (A) comprises constituting units represented by formula 3 in an amount of 45% by mass or more.

5. The cosmetic composition according to claim 1, wherein a weight-average molecular weight of Component (A) is 5,000 to 500,000.

6. The cosmetic composition according to claim 1, further comprising ethanol.

7. The cosmetic composition according to claim 1, formulated as a hair cosmetic.

8. A method of hair styling, comprising applying the cosmetic composition as defined in claim 1 to hair.

9. The cosmetic composition according to claim 1, wherein a mass ratio of Component (A) to Component (B) (Component (A)/Component (B)) is 0.8 to 1.5.

\* \* \* \* \*